United States Patent [19]

Himelstein

[11] Patent Number: 5,039,402
[45] Date of Patent: Aug. 13, 1991

[54] WATER PURIFIER

[76] Inventor: Walter D. Himelstein, P.O. Box 662, Beltsville, Md. 20705

[21] Appl. No.: 436,659

[22] Filed: Nov. 15, 1989

[51] Int. Cl.$^5$ .............................................. C02F 9/00
[52] U.S. Cl. ................................. 210/121; 210/257.1; 210/258; 210/259; 210/266; 210/284
[58] Field of Search ............ 210/121, 175, 182, 257.1, 210/259, 266, 284, 900, 258

[56] References Cited

U.S. PATENT DOCUMENTS

| | | | |
|---|---|---|---|
| 3,276,458 | 10/1966 | Iversen et al. | 210/900 |
| 3,950,253 | 4/1976 | Stern | 210/282 |
| 4,141,686 | 2/1979 | Lewis | 250/436 |
| 4,196,081 | 4/1980 | Pavia | 210/94 |
| 4,474,620 | 10/1984 | Hall | 210/257.1 |
| 4,502,953 | 3/1985 | Marsh et al. | 210/94 |
| 4,659,463 | 4/1987 | Chandler et al. | 210/202 |
| 4,681,677 | 7/1987 | Kuh et al. | 210/88 |
| 4,759,844 | 7/1988 | Lipschultz et al. | 210/266 |
| 4,764,271 | 8/1988 | Acosta | 210/86 |
| 4,828,692 | 5/1989 | Peranio | 210/266 |

*Primary Examiner*—Ivars Cintins
*Attorney, Agent, or Firm*—Wigman & Cohen

[57] ABSTRACT

A portable, household water purifier is disclosed. The water purifier generally comprises a housing adapted to rest on a kitchen counter-top, a tank mounted inside the housing for receiving untreated water, a water treatment system mounted inside the housing, a means for pumping the water through the treatment system, and a means for refrigerating the treated water.

8 Claims, 1 Drawing Sheet

5,039,402

WATER PURIFIER

BACKGROUND OF THE INVENTION

This invention relates to a water purification apparatus, and more particularly to water purifiers for household use which are portable, self-contained, and do not require connection to plumbing.

A variety of household devices for obtaining purified water exist in the art. Typically, those devices require connection to a municipal water supply in order to provide pressure to force the water through the filter media. U.S. Pat. Nos. 4,681,677 to Kuh, and 4,502,953 to Marsh are examples of such systems. Systems which must be attached to a tap or plumbing, however, have been found to be expensive to install and maintain, and are obviously unsuitable for use outside the home. Moreover, emergency situations may arise in which the pressure of the municipal water supply may be interrupted, rendering such devices inoperative.

While several domestic water purifiers which require no connection to plumbing have been placed on the market, each of those devices has been found to be deficient in several respects. The BRITA TM brand water filter system, for example, is representative of a class of portable devices which utilize gravity to draw water through a filter cartridge containing activated carbon and an ion exchange resin. However, because the water drips through the filter at an extremely slow rate, the available supply of purified water at any given time is limited.

The REGAL PUREWATER TM system is representative of another type of a domestic water purifier which includes an electric heating element that heats the water to kill bacteria. In addition to being slow-acting, the water emitted by the device is hot and therefore usually must be cooled prior to use.

U.S. Pat. No. 3,950,253 to Stern discloses a domestic water filtration apparatus which does not require connection to a municipal water supply and which avoids many of the disadvantages of the aforementioned prior art portable devices. The apparatus disclosed in the Stern patent utilizes an electric pump for positively pumping untreated water from a reservoir compartment through a filter medium and into a beaker. Although the purification process is relatively rapid compared with prior art drip-through systems, the heat generated by the electric pump renders the purified water somewhat tepid, thereby requiring removal of the beaker and separate refrigeration of the water prior to consumption as drinking water.

A further disadvantage of the apparatus disclosed in the Stern patent is the fact that the electric pump, once energized, continues to operate until de-energized by the user. Hence, the user must stand by the machine and wait until the purification process is complete to turn off the pump when the reservoir is empty.

SUMMARY AND OBJECT OF THE INVENTION

In view of the foregoing, it should be apparent that a need still exists in the art for a household water purifier that avoids the problems inherent in the prior art systems and which will rapidly supply a volume of chilled water ready for consumption as drinking water.

Accordingly, it is a primary object of this invention to provide a household water purifier that is portable, compact, easy to use and install, and which does not require connection to a municipal water supply.

Another object of this invention is to provide a household water purifier that has a relatively high flow rate compared with prior art drip-through devices.

Yet another object of this invention is to provide a household water purifier that will supply a volume of chilled water ready for consumption as drinking water without the need for separate refrigeration.

A further object of this invention is to provide a household water purifier that will efficiently filter organic material from the water, reduce the mineral content and kill bacteria therein.

Still another object of this invention is to provide a household water purifier that is contained in a portable housing, the size and shape of a typical home coffee-maker, and which is designed for kitchen counter-top use without sink hook-ups, plumbing connection or other installation.

Yet another object of this invention is to provide a water purifier which is lightweight and suitable for use away from the home such as travel to areas without adequate municipal water treatment facilities or for camping and the like.

Still another object of this invention is to provide a household water purifier having a plurality of various purification media which collectively remove most of the leading water contaminants including minerals, carcinogens, and bacteria.

Yet another object of this invention is to provide a household water purifier wherein the purification media are easily replaced or recharged.

Still another object of this invention is to provide an electrically powered water purifier with means for automatic shut-off upon completion of the purification process.

These and other objects and advantages that may become apparent hereinafter are accomplished in accordance with this invention by providing a compact housing containing a tank that may be filled with water to be purified. A small electric pump mounted in the housing pumps water from the tank through a dual chamber filter containing activated carbon and an ion exchange medium, such as a suitable resin. The water then moves through a quartz tube wherein it is radiated with ultraviolet light of a wavelength sufficient to kill bacteria. The water flows into a receiving container which rests upon a cold plate for cooling the water until the container is removed by the user. A float switch is provided in the tank for automatically terminating operation of the pump and light when the water is emptied from the tank.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF A PREFERRED EMBODIMENT

Figure 1:
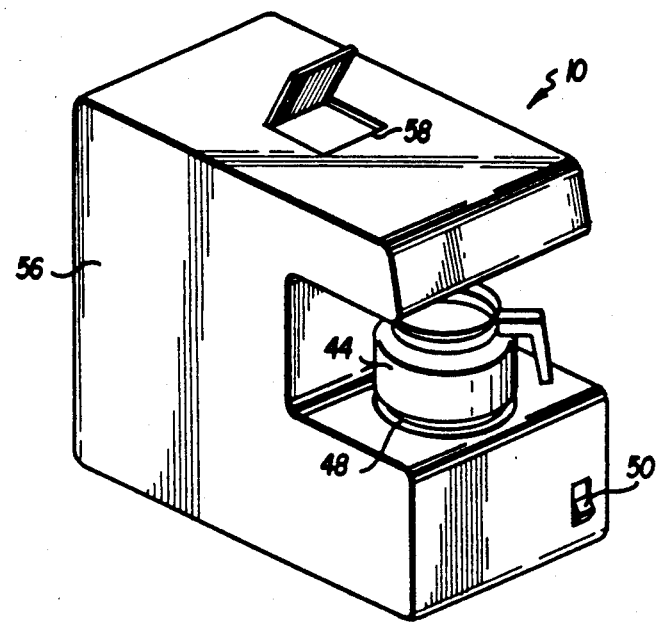
FIG. 1 is a perspective view showing the water purification apparatus of the present invention.

Referring now in detail to the drawings wherein like parts are designated by like reference numerals throughout, there is illustrated in FIG. 1 a perspective view of the water purifier of the present invention designated generally by reference numeral 10. The water purifier 10 is comprised of a generally "C" shaped housing 56, of a size and shape similar to a standard household coffee maker. It is a particular feature of the present invention that the housing 56, preferably constructed of plastic, allows the device to fit easily and inconspicuously on a kitchen counter or the like. In other words, it is designed to look like any typical kitchen appliance. Untreated water is poured into an inlet 58, a switch 50 is activated, and the water is pumped through a plurality of filtration and purification means which will be described in detail hereinafter. The purified water is collected in a receiving container 44 and is cooled by means of a cold plate 48 until the container 44 is removed by the user.

Figure 2:
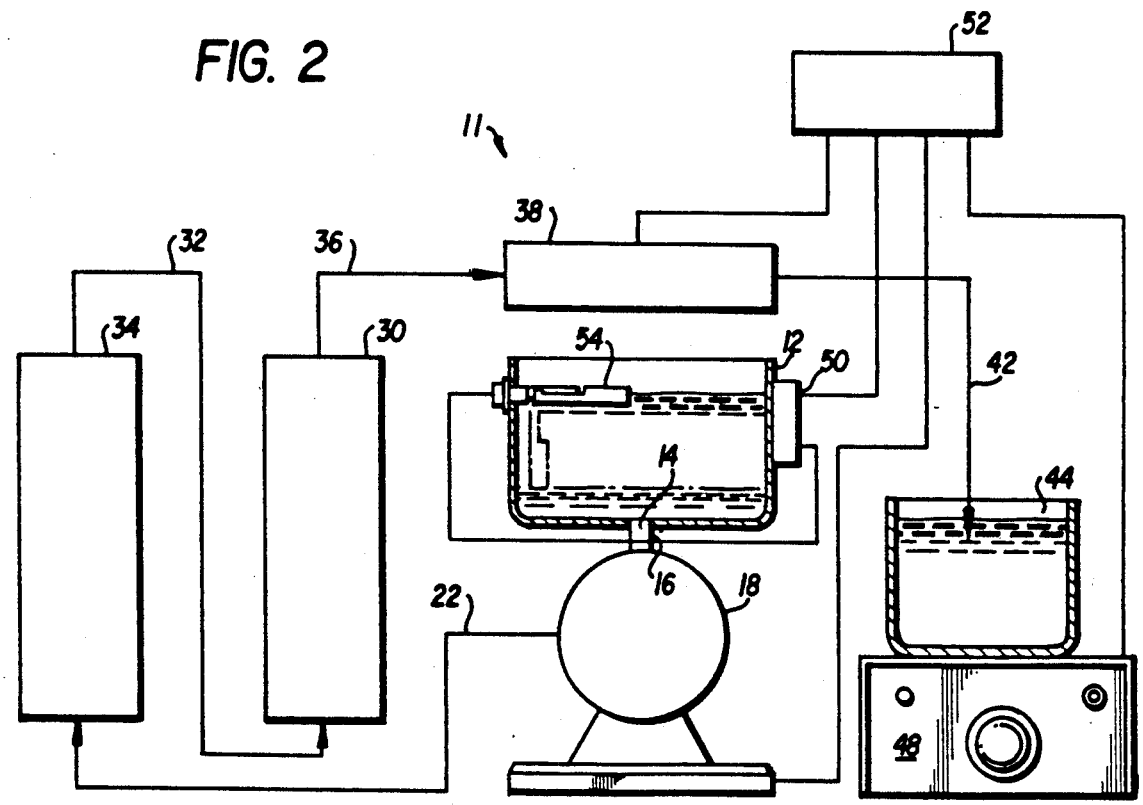
FIG. 2 is a schematic diagram of the water purification apparatus of the present invention.

Mounted within housing 56 is a purification system, designated generally by reference numeral 11 (FIG. 2). The system 11 includes a water tank 12 for collecting and storing untreated water, a water pump 18, a plurality of purification means 24, 30, and 38, the receiving container 44 and the cold plate 48.

More particularly, tank 12 is provided at the bottom with an outlet 14. A conduit 16 is connected at its first end to outlet 14 and at its second end to a water pump 18. A tube 22 is connected at its first end to the outlet of pump 18 and at its second end to the inlet of first water treatment chamber 24. Mounted within water treatment chamber 24 is an ion exchange bed consisting of a suitable resinous material.

Extending from the outlet of the first water treatment chamber 24 to the inlet of the second water treatment chamber 30 is tube 32. Mounted within chamber 30 is an activated carbon water treatment medium.

Tube 36 connects the outlet of chamber 30 to ultraviolet sterilizer 38. Sterilizer 38 is comprised of a quartz tube that will transmit ultraviolet light at a wavelength sufficient to kill bacteria. Tube 42 extends from the ultraviolet sterilizer 38 to a receiving container 44 as shown in the drawing.

The cold plate 48 is provided as a base for receiving container 44. The cold plate 48 is comprised of solid state thermoelectric modules to which DC power is applied. Air cooling or tap water may be used as the heat exchanger. The Thermoelectrics Unlimited, Inc. Model TCP-2 thermoelectric cold plate is typical of the type of plate which may be employed.

An electrical momentary switch 50 is connected to a power source 52, pump 18, cold plate 48, and sterilizer 38. A float switch 54 is preferably mounted inside water tank 12. The IMO GEMS ™ LS-7 series level switch is an example of a float switch which may be utilized.

In the use and operation of the present invention, ordinary tap water is poured into water tank 12 via inlet 58. As the water fills the tank 12, float switch 54 rises to the horizontal position illustrated by the solid lines in FIG. 2. In this position the circuit between the power source 52 and the pump 18, light 38, and cold plate 48 is closed thereby allowing the apparatus to operate upon activation of switch 50 by the user. Momentary switch 50 is actuated by the user thereby activating pump 18. Gravity forces the water in tank 12 into pump 18 via outlet 14 and conduit 16. The water is pumped, preferably at a rate of at least one liter per minute, through tube 22 into the first water treatment chamber 24 containing an ion exchange bed which removes minerals such as calcium and magnesium (i.e., "softens" the water). The water next flows into the second treatment chamber 30 containing activated carbon for removing unpleasant orders, tastes, and selected carcinogens. The water then flows into the ultraviolet sterilizer 38 where it is irradiated. As the water exits the sterilizer it is guided into receiving container 44 via tube 42. Cold plate 48 which was actuated when momentary switch 50 was activated cools the water contained in the receiving container.

When the water is emptied from the tank, gravity forces the float switch 54 to a generally vertical position (as illustrated by the phantom lines in FIG. 2). In this position the circuit between the power source 52 and the pump and ultraviolet light is opened thereby terminating the operation of each of those devices.

In sum, the above-described invention has several important advantages over the prior art. First, due to the addition of pump 18, water may be treated at a minimum rate of one liter per minute, significantly faster than the prior art drip-through system. Second, the addition of cold plate 48 obviates the need for ice or separate refrigeration. Third, because all of the internal apparatus 11 is self-contained in housing 56, no connection to plumbing is required and the device may be easily used while traveling, camping, etc. Fourth, the addition of the float switch 54 allows the user to walk away from the device after activating it since the pumping operation cuts-off automatically when the water tank is empty.

Although only a preferred embodiment of the invention is specifically illustrated and described herein, it will be appreciated that many modifications and variations of the invention are possible in light of the above teachings and within the purview of the appended claims without departing from the spirit and intended scope of the invention.

What is claimed is:

1. A portable, household water purifier comprising:
   a housing adapted to rest on a kitchen counter-top;
   a tank mounted in said housing for receiving water to be treated;
   water treatment means mounted in said housing for purifying the water contained in said tank;
   a container for receiving and retaining the treated water;
   means for pumping the water from said tank, through said treatment means, and into said container;
   refrigeration means mounted on said housing for cooling the treated water contained in said container; and
   means for automatically terminating operation of said pumping means when the water level in said tank falls to a predetermined level.

2. The water purifier of claim 1, wherein said treatment means includes a chamber containing an activated carbon bed for removing from the water unpleasant odors, taste, and selected carcinogens.

3. The water purifier of claim 1, wherein said treatment means includes a chamber containing an ion exchange material for removing unwanted minerals from the water.

4. The water purifier of claim 1, wherein said treatment means includes means to transmit ultraviolet light for bacteria destruction.

5. The water purifier of claim 4, wherein said termination means comprises a float switch mounted inside said tank for terminating operation of said pumping means and said light transmitting means when the water level in said tank falls to a predetermined level.

6. The water purifier of claim 4 wherein said light transmission means consists of a quartz tube.

7. The water purifier of claim 1 wherein said receiving container is a pitcher.

8. The water purifier of claim 1 wherein said refrigeration means consists of a cold plate.

* * * * *